(12) United States Patent
Wassermann et al.

(10) Patent No.: US 10,954,546 B2
(45) Date of Patent: Mar. 23, 2021

(54) METHOD FOR PATHOGEN ISOLATION (71) Applicant: AIT Austrian Institute of Technology GmbH, Vienna (AT)

(72) Inventors: Klemens Wassermann, Vienna (AT); Johannes Peham, Vienna (AT); Herbert Wiesinger-Mayr, Schlüsslberg (AT); Christa Nöhammer, Vienna (AT)

(73) Assignee: AIT Austrian Institute of Technology GmbH, Vienna (AT)

( * ) Notice: Subject to any disclaimer, the term of this patent is extended or adjusted under 35 U.S.C. 154(b) by 0 days.

(21) Appl. No.: 14/915,636

(22) PCT Filed: Sep. 24, 2014

(86) PCT No.: PCT/EP2014/070353
§ 371 (c)(1),
(2) Date: Feb. 29, 2016

(87) PCT Pub. No.: WO2015/044191
PCT Pub. Date: Apr. 2, 2015

(65) Prior Publication Data
US 2016/0222431 A1 Aug. 4, 2016

(30) Foreign Application Priority Data
Sep. 24, 2013 (EP) .................................. 13185831

(51) Int. Cl.
*C12Q 1/24* (2006.01)
*C12N 13/00* (2006.01)
*G01N 33/02* (2006.01)
*G01N 33/68* (2006.01)
*C12M 1/00* (2006.01)

(52) U.S. Cl.
CPC .............. *C12Q 1/24* (2013.01); *C12M 47/06* (2013.01); *C12N 13/00* (2013.01); *G01N 33/02* (2013.01); *G01N 33/6893* (2013.01); *G01N 2800/26* (2013.01)

(58) Field of Classification Search
None
See application file for complete search history.

(56) References Cited

U.S. PATENT DOCUMENTS

| | | | |
|---|---|---|---|
| 5,587,058 A * | 12/1996 | Gorodetsky | C25B 11/0484 204/290.09 |
| 6,534,295 B2 | 3/2003 | Tai et al. | |
| 8,278,041 B2 * | 10/2012 | Levin | C12Q 1/04 435/6.1 |
| 2003/0075446 A1 | 4/2003 | Culbertson et al. | |
| 2006/0289341 A1 * | 12/2006 | Muller | B03C 5/005 209/210 |
| 2012/0276635 A1 | 11/2012 | Lu et al. | |
| 2013/0273640 A1 * | 10/2013 | Krishnan | B01D 57/02 435/270 |

FOREIGN PATENT DOCUMENTS

| | | |
|---|---|---|
| WO | 1999/011771 | 3/1999 |
| WO | 2000/037163 | 6/2000 |
| WO | 2003/093791 A2 | 11/2003 |
| WO | 2005/083078 A1 | 9/2005 |
| WO | 2006/004558 A1 | 1/2006 |
| WO | 2006/092278 A1 | 9/2006 |
| WO | 2009/015484 A1 | 2/2009 |
| WO | 2011/124653 A1 | 10/2011 |
| WO | 2012/168003 A1 | 12/2012 |
| WO | 2013/013304 A1 | 1/2013 |

OTHER PUBLICATIONS

Ferré, Simon, et al. "Comparative study of SiO 2, Si 3 N 4 and TiO 2 thin films as passivation layers for quantum cascade lasers." Optics express 24.21 (2016): 24032-24044 (Year: 2016).*
Aronsson et al, "Inactivation of microorganisms using pulsed electric fields: the influence of process parameters on *Escherichia coli*, *Listeria innocua*, *Leuconostoc mesenteroides* and *Saccharomyces cerevisiae*", 2001 Innovative Food Science & Emerging Technologies 2, 41-54.
Bao et al, "Microfluidic electroporation of tumor and blood cells: observation of nucleus expansion and implications on selective analysis and purging of circulating tumor cells", Integr Biol (Camb), 2010, 2 (2-3), pp. 113-120.
Healy, Daniel "New and Emerging Therapies for Sepsis", Pharmacother. 36 (4), pp. 648-654, 2002.
Hulsheger et al, "Lethal Effects of High-Voltage Pulses on *E. coli* K12*", Radiation and environmental biophysics, Springer Verlag, DE, vol. 18, Jan. 1, 1980, pp. 281-288.
Lee et al, "A micro cell lysis device," 1999 A micro cell lysis device. Sensors and Actuators: Phys. 73, pp. 74-79.
Rangel-Frausto et al, The Natural History of the Systemic Inflammatory Response Syndrome (SIRS):, JAMA 273: 117-23, 1995.
Shah et al, "Controlled electroporation of the plasma membrane in microfluidic devices for single cell analysis", Biomicofluidics 6, 014111-1 to 014111-10, 2012.
Weaver et al, "Theory of electroporation: A review", Bioelectrochemistry and Bioenergetics 41, pp. 135-160, 1996.
Weinstein et al, "The Clinical Significance of Positive Blood Cultures in the 1990s: A Prospective Comprehensive Evaluation of the Microbiology, Epidemiology, and Outcome of Bacteremia and Fungemia in Adults", Clinical Infectious Diseases 24: 584-602, 1997.
International Search Report and Written Opinion for PCT/EU14/70353 dated Dec. 10, 2014; 11 pages.
Extended European Search Report for 13185831.8 dated Nov. 22, 2013; 6 pages.

* cited by examiner

*Primary Examiner* — Emily A Cordas
(74) *Attorney, Agent, or Firm* — Loza & Loza, LLP; Michael F. Fedrick (57) ABSTRACT

The present invention relates to methods and apparatus for detecting one or more pathogens in one or more biological samples. The biological sample may be a food sample, a sample of a body fluid, a cell suspension, water, or a combination thereof. The present invention relates also to methods of diagnosing or predicting a disease in an individual.

9 Claims, 5 Drawing Sheets

METHOD FOR PATHOGEN ISOLATION

CROSS-REFERENCE TO RELATED APPLICATIONS

This application is the U.S. national stage of International Patent Application No. PCT/EP2014/070353, filed on Sep. 24, 2014 and entitled METHOD FOR PATHOGEN ISOLATION, which claims the benefit of priority under 35 U.S.C. § 119 from European Patent Application No. 13185831.8, filed Sep. 24, 2013. The disclosures of the foregoing applications are incorporated herein by reference in their entirety.

FIELD OF THE INVENTION

The present invention relates to methods and apparatus for detecting one or more pathogens in one or more biological samples. The biological sample may be a food sample, a sample of a body fluid, a cell suspension, water, or a combination thereof. The present invention relates also to methods of diagnosing or predicting a disease in an individual.

BACKGROUND ART

Despite unprecedented progress in measurement techniques for biological analytes in recent years and the urgent need for sensitive, fast and automated diagnostic devices, most developments failed due to both low sensitivity and complex, expensive multi-step sample preparation, especially regarding high-complex biological samples. As a consequence, lengthy and labor intensive diagnostic procedures still have to be done by highly skilled professionals, for instance infection diagnostics from blood. Here, the blood culture method is still the gold standard for the detection of pathogenic bacteria from blood but due to its long time-to-results (typically 3-5 days) nucleic acid-based techniques (NAT), such as Roche's SeptiFAST, have recently been accepted as alternatives. These sequence-specific NAT methods especially rely on thorough sample preparation including lysis of cells and purification of DNA.

There are different strategies for sample preparation such as unspecific whole sample lysis by chemical, enzymatical, mechanical or thermal means. However, the high background of non-target molecules resulting from whole sample lysis of complex samples such as whole blood interferes with a sensitive detection of low-abundant target molecules. To reduce the background, capture of target analytes prior to lysis by antibody coated surfaces or micro-beads, filters or dielectrophoresis is another strategy for sample preparation. WO2013013304A1 comprises a so-called capture zone to capture and concentrate target cells prior to electrically assisted thermal lysis. Additionally, WO00037163A1 describes a system for separation of prokaryotic and eukaryotic cells from a mixed cell suspension by dielectrophoresis. In complex samples such as blood, however, besides omitting intracellular pathogens, these methods raise problems regarding epitope-screening, costs and shelf life of antibody-dependent capture methods, clogging of filters or reproducibility and complexity of dielectrophoretic methods. A third strategy is to actively remove or reduce the non-target background, such as eukaryotic cells or DNA for the detection of pathogenic bacteria. One prominent example is the MOLYSIS™ kit from Molzym (WO2006092278A1) which uses chaotropic salts and/or one or several surfactants to lyse eukaryotic cells in combination with DNA-degrading nucleases. Other methods for eukaryotic specific lysis are depicted in WO2012168003A1 and WO2009015484A1 which use ionic surfactants or saponines, respectively. Alternatively, WO2011124653A1 describes the separation of viral and/or prokaryotic nucleic acids at least partially from eukaryotic nucleic acids after whole sample lysis. Together, these methods of cell-specific sample preparation tend to be costly, complex and require multistep protocols, which challenge their automation and integration capability into diagnostic devices.

In contrast, lysis of cells by electrical fields has the potential to be rapid, cost effective and capable of being integrated and automated. The effect of electrical fields on cells is well known (Weaver, Chizmadzhev, 1996) and applied for the transport of different molecules into cells (reversible electroporation), as well as for cell lysis (irreversible electroporation). Different susceptibilities of cells and cell-organelles to electric fields could be shown (Bao, Le, Cheng, Lu, 2010; Shah, Steffen, Lilge, 2012; Aronsson, Lindgren, Johansson, Rönner, 2001), but to the best of our knowledge, cell-specific lysis by electrical fields in a diluted or undiluted biological sample has never been shown. For instance, WO2003093791A2 and WO2005083078A1 describe the use of electrical fields for unspecific lysis of cells in biological samples and in US20120276635A1 unspecific lysis of cells in a microfluidic channel by applying a direct current is described. Additionally, WO0037163A1, WO2006004558A1 and U.S. Pat. No. 6,534,295B2 use dielectrophoresis prior to electrical lysis to gain specificity.

WO9911771A1 discloses a method for cell separation by subjecting a sample of purified and rebuffered cells to an electric field of a magnitude sufficient to porate a substantial fraction of cells and inactivating all the porated cells and select the viable subpopulation. The method may be used for stem cell enrichment/isolation and cancer cell purging.

For the development of sensitive, rapid and automated diagnostic devices, especially in regards to infectious disease testing from blood, new sample preparation methods are urgently needed. Eukaryotic-specific electrical lysis in biological samples would reduce the background of eukaryotic material, resulting in a significant increase of sensitivity, which is essential for diagnostics. Furthermore, this approach enables low production and running costs, is compatible with batch and flow-through processing and can be easily automated and integrated Early detection of a disease condition typically allows for a more effective therapeutic treatment with a correspondingly more favorable clinical outcome. In many cases, however, early detection of disease symptoms is problematic; hence, a disease may become relatively advanced before diagnosis is possible. Systemic inflammatory conditions represent one such class of diseases. These conditions, particularly sepsis, typically result from an interaction between a pathogenic microorganism and the host's defense system that triggers an excessive and dysregulated inflammatory response in the host. The complexity of the host's response during the systemic inflammatory response has complicated efforts towards understanding disease pathogenesis (Healy, Annul. Pharmacother. 36: 648-54 (2002)). An incomplete understanding of the disease pathogenesis, in turn, contributes to the difficulty in finding diagnostic biomarkers. However, early and reliable diagnosis is imperative because of the remarkably rapid progression of sepsis into a life-threatening condition.

Sepsis follows a well-described time course, progressing from systemic inflammatory response syndrome (SIRS)- negative to SIRS-positive to sepsis, which may then progress to severe sepsis, septic shock, multiple organ dysfunction (MOD), and ultimately death. Sepsis is commonly defined as SIRS with a confirmed infectious process.

Documenting the presence of the pathogenic microorganisms clinically significant to sepsis, however, has proven difficult. Causative microorganisms typically are detected by culturing a patient's blood, sputum, urine, wound secretion, in-dwelling line catheter surfaces, etc. Besides the long time to result, low numbers of pathogens in blood present a particular problem for diagnosing sepsis by culturing blood. In one study, for example, positive culture results were obtained in only 17% of patients presenting clinical manifestations of sepsis (Rangel-i Frausto et al., JAMA 273: 117-23 (1995)). Diagnosis can be further complicated by contamination of samples by non-pathogenic microorganisms. For example, only 12.4% of detected microorganisms were clinically significant in a study of 707 patients with septicemia (Weinstein et al., Clinical Infectious Diseases 24: 584-602 (1997).) The difficulty in early diagnosis of sepsis is reflected by the high morbidity and mortality associated with the disease. Sepsis currently is the tenth leading cause of death in the United States and is especially prevalent among hospitalized patients in non-coronary intensive care units (ICUs), where it is the most common cause of death. The overall rate of mortality is as high as 35% with an estimated 750,000 cases per year occurring in the United States alone. The annual cost to heal sepsis in the United States alone is in the order of billions of dollars.

Thus, early diagnosis of an infection which could cause a septic syndrome is essential and makes it possible to propose a treatment which is suited to the patient.

A need, therefore, exists for a method of diagnosing sepsis and other infectious diseases sufficiently early to allow effective intervention and prevention.

Diagnostic strategies incorporating molecular-biology based techniques have recently been developed to detect pathogenic infection of biological samples. These methods, however, rely on thorough sample preparation especially as the high non-target background of most biological samples challenges the sensitivity and specificity of such assays.

The object of the present invention was to find a new sample preparation method for cell type specific lysis of cells in a biological sample to enable separation and detection of pathogens.

The object is achieved by the provision of the embodiments of the present invention.

SUMMARY OF INVENTION

The present invention relates to a method for targeted lysis of cells in a biological sample containing a pathogen, wherein said biological sample is exposed to an electric field and wherein only non-pathogenic cells are lysed. The intact pathogenic cells are separated and determined, thus allowing early detection of the presence of a pathogen in said biological sample.

DESCRIPTION OF EMBODIMENTS

There is still a continuing urgent need in the art to diagnose infectious diseases, with specificity and sensitivity, without the need for monitoring a patient over time. Ideally, diagnosis would be made by a technique that accurately, rapidly, and simultaneously measures a plurality of biomarkers at a single point in time, thereby minimizing disease progression during the time required for diagnosis.

Thus, the present invention relates to a method for targeted lysis of cells in a biological sample optionally containing a pathogen, wherein said biological sample is exposed to an electric field and whereupon non-pathogenic cells are lysed.

A further aspect of the invention is a method of isolating and/or concentrating a pathogen in a biological sample comprising:
 a. exposing said biological sample optionally comprising a pathogen to an electric field of a magnitude that selectively non-pathogenic cells in said sample are lysed; and
 b. collecting the intact pathogenic cells.

One aspect of the invention is the method as described above wherein said non-pathogenic cells are eukaryotic cells stemming from host material, e.g. from whole blood, tissue, urine, saliva, food, cell cultures, water, etc. or a combination thereof.

Another aspect of the invention is the method as described above, wherein the biological sample is selected from the group consisting of whole blood, urine, saliva, tissue, cell cultures, water and food. Preferably the biological sample is a whole blood sample from a patient. A biological sample may also be any material which is derived from a patient, in particular, be a sample of blood, of saliva, of tissue or of circulating cells from the patient. This biological sample is obtained by any type of withdrawal known to the skilled person, such as, in particular, taking a blood sample.

One aspect of the invention is the method as described above wherein said pathogen is a bacterium, a protozoa or a fungus. In a preferred embodiment, the pathogen is a bacterium.

In another aspect of the invention, the biological sample comprising the host material and pathogenic cells may be used without any pretreatment procedure, thus no prior cell separation step such as centrifugation or affinity binding techniques have to be applied. In particular, the biological sample can be applied without any preliminary cell isolation step.

In a further aspect, the biological sample may be diluted or undiluted before it is subject to the inventive method.

According to a further aspect of the invention there is provided a means to expose the biological sample to a variable electric or electromagnetic field comprising: at least a first and a second electrode and a control means for applying a variable potential to the first and second electrodes, whereby non-pathogenic cells within the electric field are lysed and pathogenic cells remain unharmed. The field strength may be chosen according to the nature of the non-pathogenic cells, and the proportions of non-pathogenic and pathogenic cells that are to be destroyed on average in a given treatment.

In a further object of the invention, the eukaryotic host cells are lysed by said electric field, whereas prokaryotic cells or other pathogens are not lysed. In particular, the lysis operation is selective to cells from host components, e.g., blood cells, cells from tissue, urine, saliva, or eukaryotic cells from food or cell cultures. The pathogenic agent cells are not lysed. It is one further aspect of the invention to provide an electrical field high enough to affect only the cell membrane of non-pathogenic cells and leave the cell membrane of the pathogenic cells intact.

As used herein, "pathogen" or "pathogenic cell" refers to a microorganism in the widest sense, such as for example a bacterium, protozoa or fungus that might cause disease in its host. The host may be an animal, including humans, or even another microorganism or cell suspensions thereof.

As used herein, "eukaryotic cells" refer to cells containing a nucleus and other organelles enclosed within membranes. There are many different types of eukaryotic cells, though animals and plants are the most familiar eukaryotes. Fungi and many protozoa also belong to eukaryotes, due to substantial differences and their respective role in infectious diseases, however, these organisms or sub-classes thereof are referred to as pathogens or pathogenic cells in this invention.

In a further aspect of the invention, the intact pathogenic cells are separated, optionally further concentrated and purified to enable their detection and identification, for instance by nucleic acid-based techniques.

In one embodiment, the purification is carried out by a centrifugation step. The separation step can be carried out to separate the intact pathogenic cells from other components of the sample (e.g., non-microorganisms or components thereof) and to concentrate the pathogenic cells for identification and characterization purposes. The separation does not have to be complete, i.e., it is not required that 100% separation occurs. All that is required is that the separation of the pathogens from other components of the sample be sufficient to permit interrogation of the pathogen without substantial interference from the other components.

In one embodiment, the separation of the infectious agent is carried out by retention means.

As used herein, "retention means" refers to filter, chromatography columns, electrophoresis and dielectrophoresis, antibody capture methods, flow separation, fluidic focusing, elutriation or size exclusion methods.

In one aspect of the invention the electric field is an alternating field. The electric field is of sufficient strength to cause electropermeabilization or electro-lysis of the non-pathogenic cells. This key aspect of the present lysis method allows for cell-type specific lysis of said cells. Specifically, the method allows lysis of non-pathogenic eukaryotic cells in a biological sample containing eukaryotic cells and pathogenic cells.

Electric fields generating transmembrane potentials of the order of 0.2-1.5V cause rupture of the lipid bilayer forming pores, and with sufficient magnitudes of electric field strengths and time of exposure lead to cell lysis. The electric field strength required to reach the threshold to promote cell lysis will thus depend on cell size and shape as well as membrane composition (fluidity). While a DC field of 7-10 kV/cm is required to lyse the smaller microbial cells, the larger plant protoplasts are lysed using only 1.5-1.75 kV/cm electric fields (Lee S. W, Tai Y. C 1999 A micro cell lysis device. Sens. Actuators A: Phys. 73, 74-79).

A different strategy to employ electrical lysis for analysis of cells is a static field or a combination of alternating current (AC) and direct current (DC) electric fields.

Another aspect of the invention is the method as described above, wherein the electric field is generated by 2D, 2.5D or 3D electrodes, preferably by parallel or 3D electrodes, including meshes.

An electrode, for example a first electrode in a pair of electrodes, may be formed from a variety of different materials. Optionally the first electrode and the second electrode are formed from the same material. Typically, the electrodes are formed from metals or alloys. The first and the second electrode may for example comprise a metal selected from the group comprising: silver, gold, platinum, copper, carbon, iron, graphite, chromium, nickel, cobalt, titanium, mercury or an alloy thereof.

Another aspect of the invention is the electric passivation of the electrode material by electrical insulating or semi-conducting materials (organic and inorganic coatings) as well as metal oxides in the lower micrometer to nanometer range. The passivation of the electrode thus prevents electrochemical effects between the electrode and the sample which otherwise will lead to undesired effects such as unspecific lysis caused by local pH changes, as well as electrode degradation. Additionally, passivation of the electrode averts joule heating, thereby further increasing lysis specificity. Additionally, electrode passivation prevents low impedance loads due to the ohmic effect of the sample and minimizes capacitive losses of the passivation itself (minimal thickness, maximum permittivity) and guarantees a sufficiently high potential difference and thereby an electric field in the sample.

Electrode passivation allows the use of different electrode base materials (copper, aluminum, gold, titanium, etc.) as well as enables the use of simple electrical circuits for capacitive loads without the need for high purely resistive currents, which have to be driven through the liquid sample and which would lead to unspecific lysis if not passivated. Furthermore, the passivation is biocompatible, which means very low binding of cells, proteins and nucleic acids, which is essential for an effective lysis and release of the analyte material.

The present invention also provides a microfluidic design including an electrolysis device for cell lysis which includes electrodes.

Thus, another aspect of the invention is the use of microfluidic design which separates the electrodes by 10 to 500 µm, preferably 20 µm to 100 µm, which allows the use of low electric potentials to generate high electric fields.

Another aspect of the invention is the method as described above, wherein the alternate electric field is in the range of about 1 GHz and 10 Hz and of about 0.5 to 20 kV/cm, preferably in the range of about 10 MHz and 10 kHz and of about 1 to 10 kV/cm, preferably 1 MHz and of about 2-4 kV/cm.

Another aspect of the invention is a method of diagnosing a disease in an individual, comprising the steps:
   a. obtaining a biological sample from said individual;
   b. conducting a method as described above, wherein non-pathogenic host cells are type specifically lysed;
   c. collecting the intact pathogenic cells;
   d. analyzing said pathogenic cells, and.
   e. obtaining a diagnostic result for initiation an effective treatment in said individual.

In another embodiment, there is provided a method of diagnosing a patient for the presence of a disease comprising obtaining a sample from said patient, conducting a method as described above, isolating the pathogenic cells from said biological sample, identifying said pathogenic cells and diagnosing the patient's condition from the identified pathogenic cells in the sample.

One embodiment of the invention is the method as described above, wherein the disease is a systemic inflammatory condition, e.g. sepsis, or an infectious disease of bacterial, fungal or protozoan origin.

The method is specifically appropriate to diagnose early sepsis. Appropriate antibiotics to treat sepsis are usually combinations of two or three antibiotics given at the same time. Once the infecting organism is isolated and identified, labs can determine which antibiotics are most effective against the organisms, and those antibiotics should be used to treat the patient.

A further embodiment of the invention is an apparatus for concentrating and purifying pathogens from a biological sample comprising an electroporation chamber, wherein said chamber has an input and output end, at least two passivated electrodes and a retention means, such as filters or cell traps.

Specifically, the apparatus comprises of at least one fluidic chamber or channel comprising at least two electrodes, where at least one electrode is passivated and with an electrode distance between 10 and 500 μm and at least one fluidic connection.

EXAMPLES

The Examples which follow are set forth to aid in the understanding of the invention but are not intended to, and should not be construed to limit the scope of the invention in any way. The Examples do not include detailed descriptions of conventional methods, e.g., cloning, transfection, and basic aspects of methods for overexpressing proteins in microbial host cells. Such methods are well known to those of ordinary skill in the art.

Example 1

Effect of Electrical Fields on DNA Carrying Human Blood Cells

Figure 1:
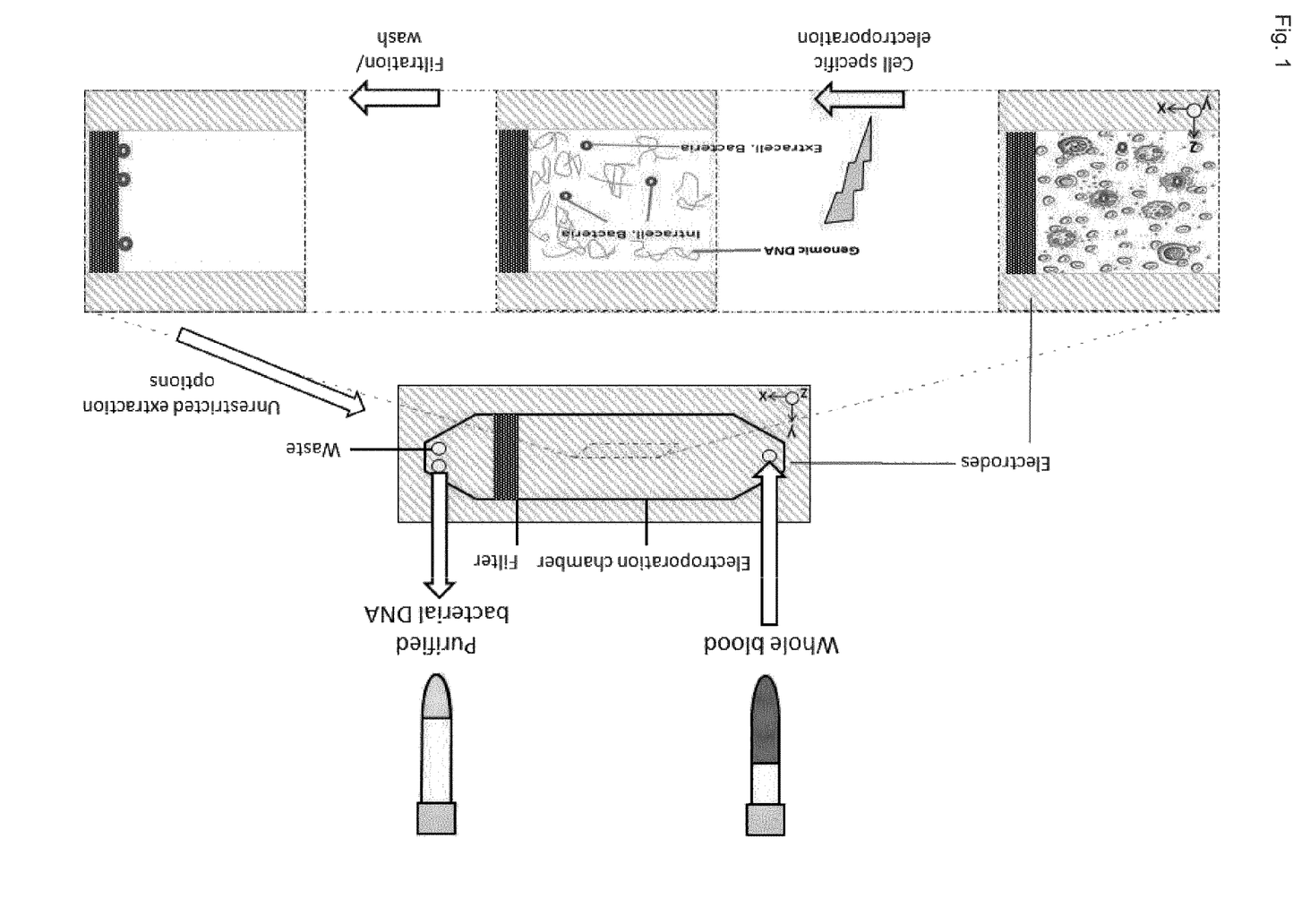
FIG. 1 shows a schematic sketch of a cell-type specific electrical sample processing device.
Figure 2:
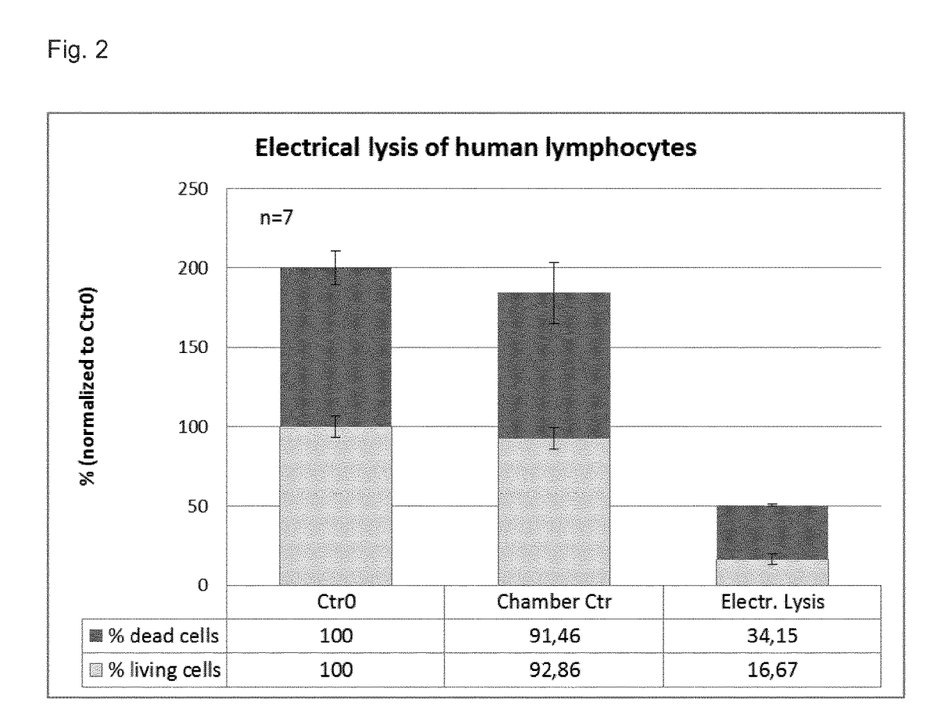
FIG. 2 illustrates the effect of electrical lysis on human lymphocytes.

The experiment demonstrates the effect of electrical fields on DNA carrying human blood cells. Human EDTA blood was withdrawn from a volunteer, treated with erythrocyte lysis buffer and subsequently centrifuged at 400 g for 5 minutes at room temperature. The cell pellet was resuspended in 250 mM sucrose in ddH$_2$O. One aliquot of the cell suspension was used for immediate viability staining and cell count (FIG. 2 Ctr0). A second aliquot was introduced to the cell lysis chamber comprising two parallel planar copper electrodes coated with polytetrafluoroethylene (PTFE) separated by a 50 μm silicone film forming a chamber for one minute followed by viability staining and cell counting (FIG. 2 Chamber Ctr). After thoroughly washing the lysis chamber, a third aliquot of the cell suspension was introduced to the cell lysis chamber and a square-pulse alternating current of 1 MHz and 10 V$_{pp}$ was applied for 1 minute for electrical lysis, followed by viability staining and cell counting (FIG. 2 Electr. Lysis).

Example 2

Cell-type Specificity of Electrical Lysis

Figure 3:
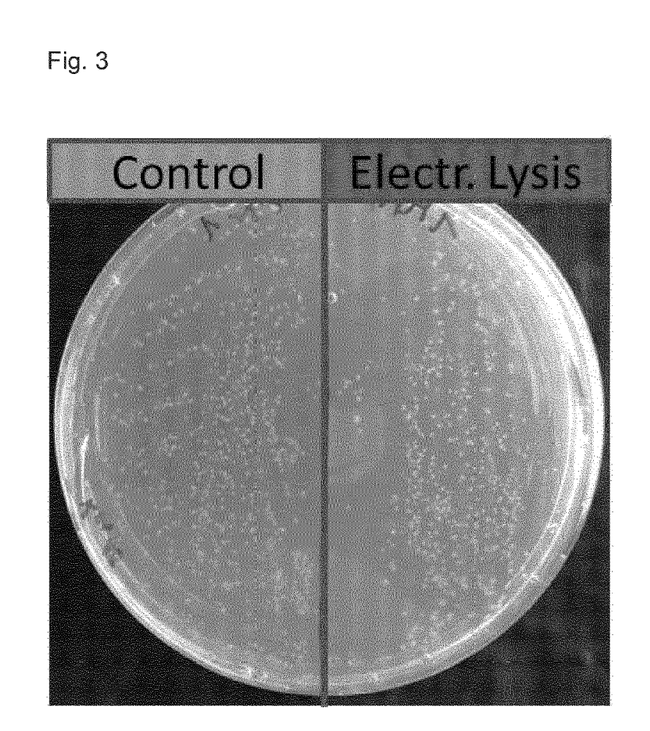
FIG. 3 shows the growth of *Escherichia coli* after electrical lysis of a mixed sample of human lymphocytes spiked with *Escherichia coli*.
Figure 4:
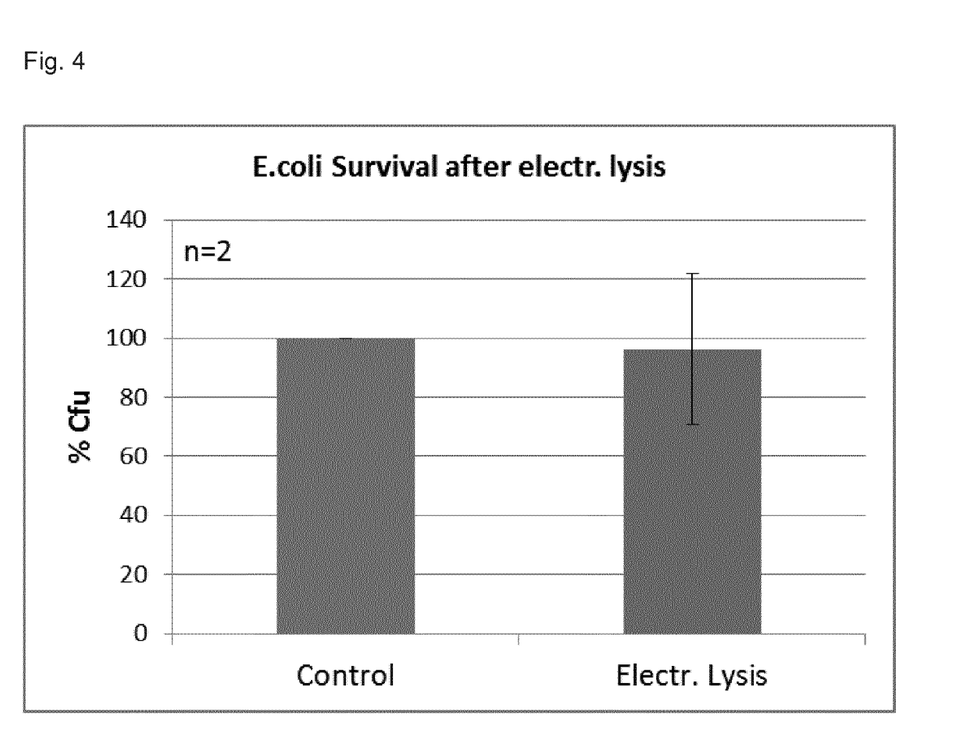
FIG. 4 shows the recovery percentage of *Escherichia coli* after electrical lysis of a mixed sample of human lymphocytes spiked with *Escherichia coli*.
Figure 5:
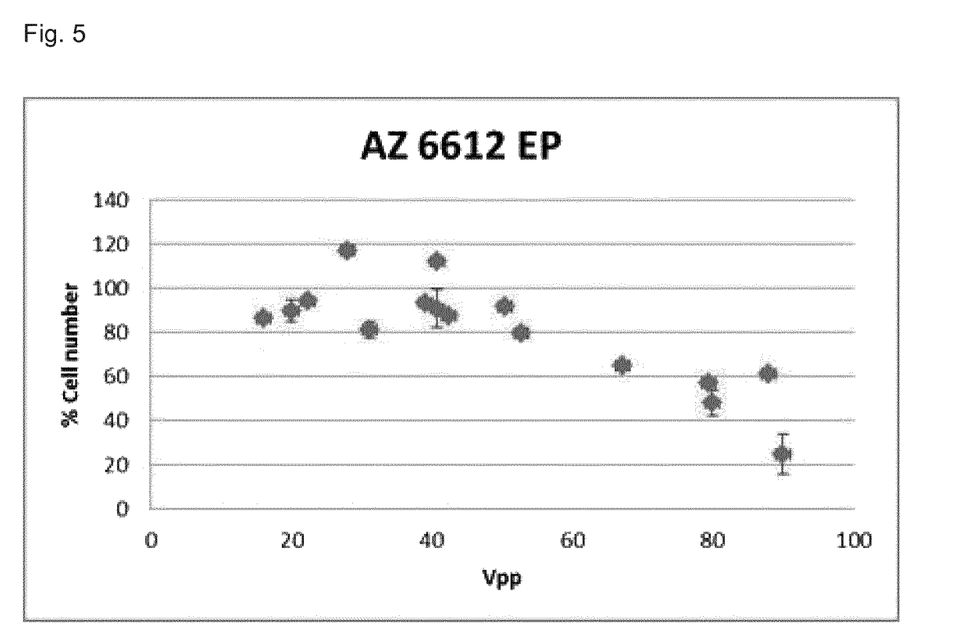
FIG. 5 shows the voltage dependence of lysis efficiency using copper electrodes with a 2 µm AZ 6612 photoresist passivation.
Figure 6:
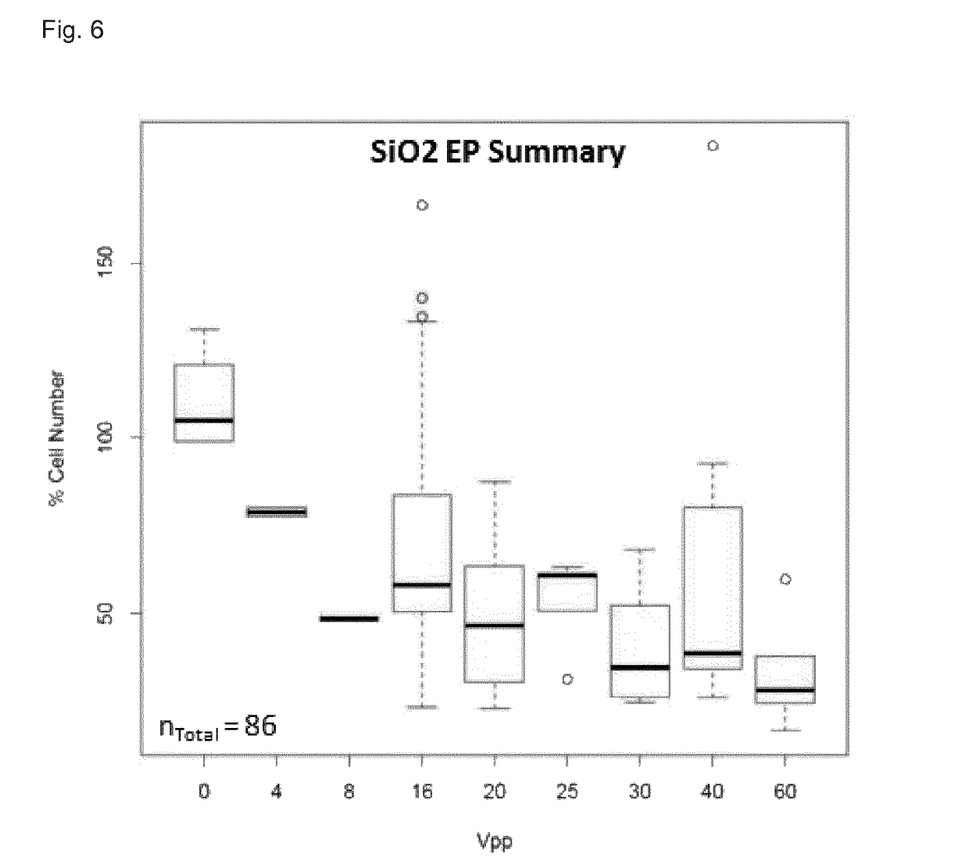
FIG. 6 illustrates the voltage dependent lysis efficiency using silicon electrodes with a 50 nm $SiO_2$ passivation.

The experiment demonstrates the cell-type specificity of electrical lysis. Human EDTA blood was withdrawn from a volunteer, treated with erythrocyte lysis buffer and subsequently centrifuged at 400 g for 5 minutes at room temperature. The cell pellet was resuspended in 250 mM sucrose in ddH$_2$O, followed by viability staining and cell counting. One aliquot was spiked with 10$^3$ Kanamycin-resistant *Escherichia coli* cells and introduced to the cell lysis chamber for one minute without applying an electric field (FIG. 3 Control). After thoroughly washing the lysis chamber, a second aliquot of the cell suspension was spiked with 10 Kanamycin-resistant *Escherichia coli* cells, introduced to the cell lysis chamber and a square-pulse alternating current of 1 MHz and 10 V$_{pp}$ was applied for one minute for electrical lysis (FIG. 3 Electr. Lysis). After lysis, both aliquots were plated on Kanamycin (50 μg/ml) lysogeny broth (LB) agar plates followed by an incubation for 18 hours at 37° C. To assure lymphocyte lysis, a third aliquot of the cell suspension was spiked with 10 Kanamycin-resistant *Escherichia coli* cells, introduced to the washed cell lysis chamber and a square-pulse alternating current of 1 MHz and 10 V$_{pp}$ was applied for 1 minute for electrical lysis. Cell viability staining and cell count confirmed unchanged lysis efficiency. After incubation, colonies on the agar plates were counted to compare *Escherichia coli* survival after electrical lysis to the control (FIG. 4). This is the first proof of principle of cell-type specific electrical lysis.

Example 3

Influence of Electrode Passivation on Electrical Lysis

Figure 7A:
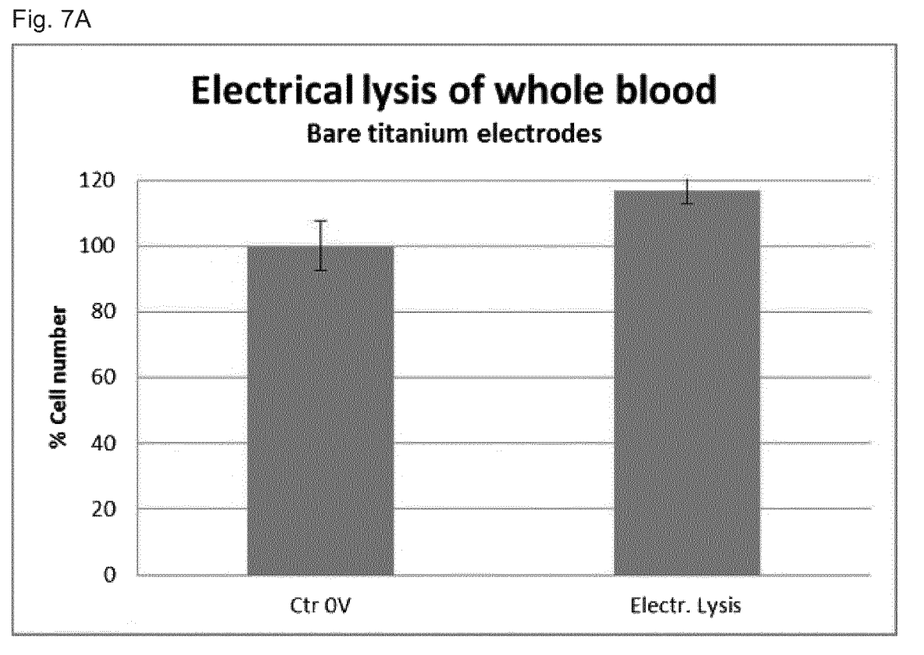
FIG. 7 shows low voltage cell lysis of whole blood using bare titanium electrodes (A) or titanium electrodes with a 500 nm $TiO_2$ passivation layer (B).
Figure 7B:
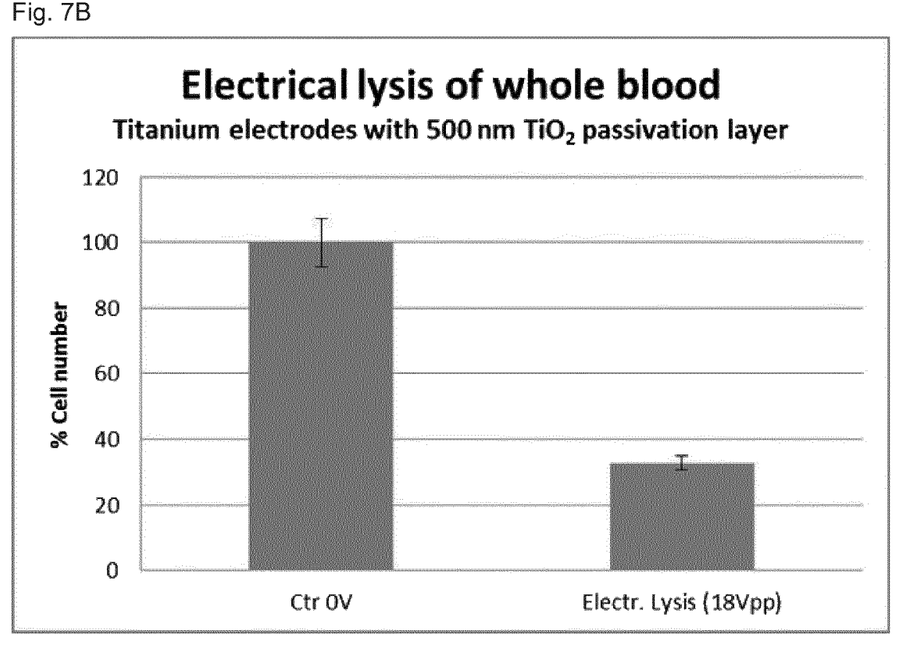

The experiment demonstrates the influence of electrode passivation on electrical lysis of whole blood cells. Grade 2 titanium foils were used as electrode material. FIG. 7A shows the results of electrical lysis without passivation layers on titanium. No lysis was observed due to a complete drop of potential due to the low impedance load caused by direct electrical contact between the electrode and the blood sample. FIG. 7B shows the results of electrical lysis with thermally oxidized titanium electrodes. Lysis and a reduction in cell number compared to control can be observed. Due to electrode passivation by a thin titanium dioxide film of 500 nm grown by thermal oxidation, direct electrical contact between the electrode and the blood sample is significantly reduced, leading to a reduction of current and high potential between the electrodes, establishing a sufficiently high electric field.

The invention claimed is:

1. A method of isolating and concentrating a pathogen from a biological sample comprising:
   a) exposing a biological sample comprising blood cells to an electric field of a magnitude whereupon selectively blood cells in said sample are lysed, wherein the electric field is generated by passivated electrodes which are spaced apart by between 20 μm and 100 μm, and wherein the electrodes are passivated by a layer of TiO$_2$ or SiO$_2$; and
   b) collecting the intact pathogenic cells,
   wherein the electric field is an alternating electric field in the range of about 10 MHz to 10 kHz and of about 1 to 10 kV/cm.

2. The method according to claim 1, wherein said pathogenic cells are selected from the group consisting of bacterial cells, protozoan cells, and fungal cells.

3. The method according to claim 1, wherein said intact pathogenic cells are detained by retention means.

4. The method according to claim 1, wherein the biological sample is a cell suspension.

5. The method of claim 1, wherein the pathogenic cells are bacterial cells.

6. A method of determining a disease in an individual, comprising:
   a) performing the method of claim 1, wherein the biological sample is obtained from the individual;
   b) identifying the intact pathogenic cells; and
   c) determining the disease in said individual from the identified pathogenic cells in the biological sample.

7. The method according to claim 6, wherein said disease is an infectious disease.

8. The method according to claim 6, further comprising the step of separating the intact pathogenic cells from the biological sample after step a).

9. The method according to claim 7, wherein said infectious disease is sepsis.

* * * * *